(12) United States Patent
Christensen et al.

(10) Patent No.: US 10,087,577 B2
(45) Date of Patent: Oct. 2, 2018

(54) SYSTEMS, DEVICES AND METHODS FOR AGRICULTURAL PRODUCT PULPING

(71) Applicant: BIO AG RESOURCES, INC., Fruitland, ID (US)

(72) Inventors: Kurt Christensen, Parma, ID (US); William Robert Charles Charlton, Boise, ID (US); Neill Goodfellow, Fruitland, ID (US); H. Charles Anderson, Boise, ID (US)

(73) Assignee: BIO AG RESOURCES, INC., Fruitland, ID (US)

(*) Notice: Subject to any disclaimer, the term of this patent is extended or adjusted under 35 U.S.C. 154(b) by 8 days.

(21) Appl. No.: 14/852,424

(22) Filed: Sep. 11, 2015

(65) Prior Publication Data

US 2016/0076198 A1     Mar. 17, 2016

Related U.S. Application Data

(60) Provisional application No. 62/049,878, filed on Sep. 12, 2014.

(51) Int. Cl.

| | |
|---|---|
| D21C 1/10 | (2006.01) |
| D21H 11/12 | (2006.01) |
| D21H 11/00 | (2006.01) |
| D21C 1/02 | (2006.01) |
| C12M 1/00 | (2006.01) |
| D21C 3/02 | (2006.01) |
| D21C 3/26 | (2006.01) |
| D21C 11/00 | (2006.01) |

(Continued)

(52) U.S. Cl.
CPC ............... D21C 1/10 (2013.01); C12M 21/04 (2013.01); C12M 21/12 (2013.01); C12M 43/00 (2013.01); C12M 45/02 (2013.01); C12M 45/04 (2013.01); C12M 45/06 (2013.01); C12M 45/20 (2013.01); D21C 1/02 (2013.01); D21C 3/02 (2013.01); D21C 3/26 (2013.01); D21C 11/0007 (2013.01); D21H 11/12 (2013.01)

(58) Field of Classification Search
CPC ....... D21C 1/10; D21C 11/0007; D21H 11/12
See application file for complete search history.

(56) References Cited

U.S. PATENT DOCUMENTS

| | | | | |
|---|---|---|---|---|
| 5,725,762 | A * | 3/1998 | Beal ................... | B01D 21/0003 110/221 |
| 6,454,944 | B1 * | 9/2002 | Raven ................... | C12M 21/04 210/180 |
| 2009/0107643 | A1 * | 4/2009 | Petit-Conil ............ | D21B 1/021 162/68 |

OTHER PUBLICATIONS

Smook, Handbook for Pulp and Paper Technologists, 1992, Angus Wilde Publications, 2nd edition, chapters 3 and 26.*

(Continued)

*Primary Examiner* — Anthony Calandra
(74) *Attorney, Agent, or Firm* — Knobbe, Martens, Olson & Bear, LLP

(57) ABSTRACT

This disclosure relates to systems, devices and methods for pulping agricultural products. Features for ensiling agricultural crops, separating solids and liquids, and processing the solids and liquids for use in a variety of products and processes are disclosed. For instance, systems and methods are disclosed for pulping grass crops, making products for energy conversion processes, screening fine debris, cell bursting, using strongly alkaline chemicals in pulping processes, and using sorghum plant for producing pulp.

28 Claims, 7 Drawing Sheets

(51) Int. Cl.
*C12M 1/107* (2006.01)
*C12M 1/33* (2006.01)

(56) References Cited

OTHER PUBLICATIONS

Meyer et al., Anaerobic digestion of pulp and paper mill wastewater and sludge, Jul. 2014, Water Research (65), p. 321-349.*
Smook, Handbook for Pulp and Paper Technologists, 1992, Angus Wilde Publications, 2nd edition, chapters 8, 9, and 13.*

* cited by examiner

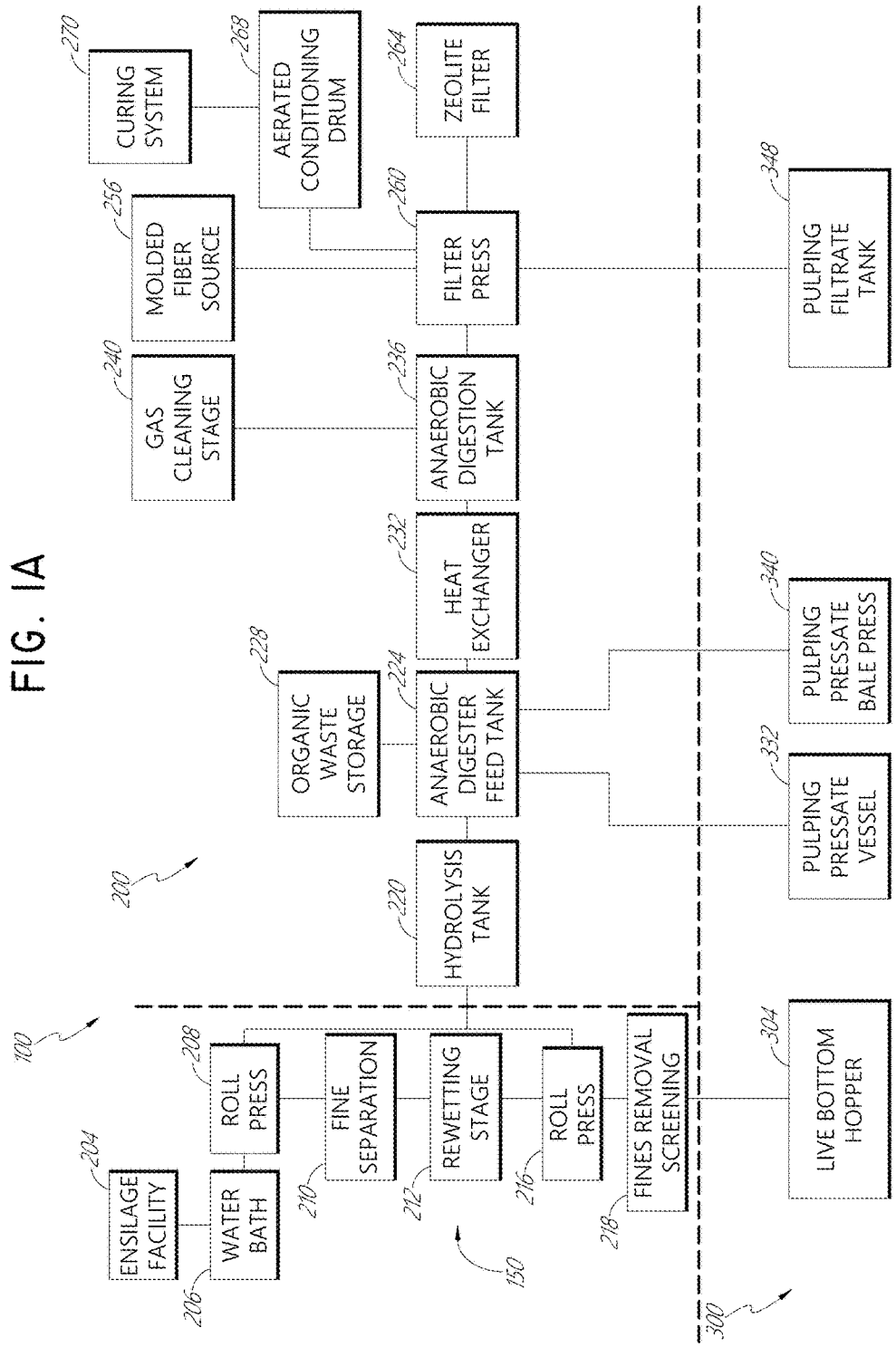

SYSTEMS, DEVICES AND METHODS FOR AGRICULTURAL PRODUCT PULPING

CROSS-REFERENCE TO RELATED APPLICATIONS

This application claims priority to U.S. Provisional Patent Application Ser. No. 62/049,878 filed on Sep. 12, 2014 and entitled "Systems, Devices and Methods for Agricultural Product Pulping", the content of which is hereby incorporated by reference in its entirety.

FIELD OF THE INVENTION

This disclosure relates generally to pulping agricultural products. In particular, systems and processes for pulping wet agricultural silage using liquid separation, screening fines, cell bursting, and alkaline chemicals are disclosed.

BACKGROUND

Agricultural crops have been used in the production of energy and other non-food products. However, it would be advantageous to increase the cost-effectiveness of biomass processing of agricultural processes. It would also be advantageous to provide valuable outputs in addition to energy.

Most paper is currently produced from trees, which grow slowly. It can take 10 years, 20 years, or more between harvest of such forest crops. Pulping processes are energy-intensive and often use bleach and other potentially harmful chemicals. Thus, it would be advantageous to use more rapidly-growing crops in the production of paper pulp and to simplify the process by which paper products are produced.

SUMMARY

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing pulping processes.

In a first aspect, systems and methods for an ensilage process for the purpose of using silage for pulping of agricultural crops are disclosed.

In another aspect, systems and methods for an ensilage process for the purpose of pulping of grass crops are disclosed.

In a further aspect, systems and methods for the separation of liquid from agricultural crops using mechanical and/or physical means for the purpose of pulp and/or energy production are disclosed.

In another aspect, systems and methods for screening of fine debris from agricultural crops for the purpose of pulp production are disclosed.

In a further aspect, systems and methods for cell burst using low to high temperature for the purpose of utilizing agricultural crops in pulp production are disclosed.

In another aspect, systems and methods for using strongly alkaline chemicals, such as Lime ($Ca(OH)_2$), Caustic Potash (KOH) and/or Caustic Soda (NaOH) and Hydrogen Peroxide to produce pulp from agricultural crops, are disclosed.

In a further aspect, systems and methods for using sorghum plant material for the production of pulp are disclosed.

BRIEF DESCRIPTION OF THE DRAWINGS

The foregoing and other features, aspects and advantages of the present invention will now be described with reference to the drawings of certain embodiments, which are intended to illustrate and not to limit the present invention.

FIG. 1A is a schematic illustration of components in an embodiment of a system for pulping agricultural products, showing mostly components of the separation stage and liquid pathway.

DETAILED DESCRIPTION

Figure 1B:
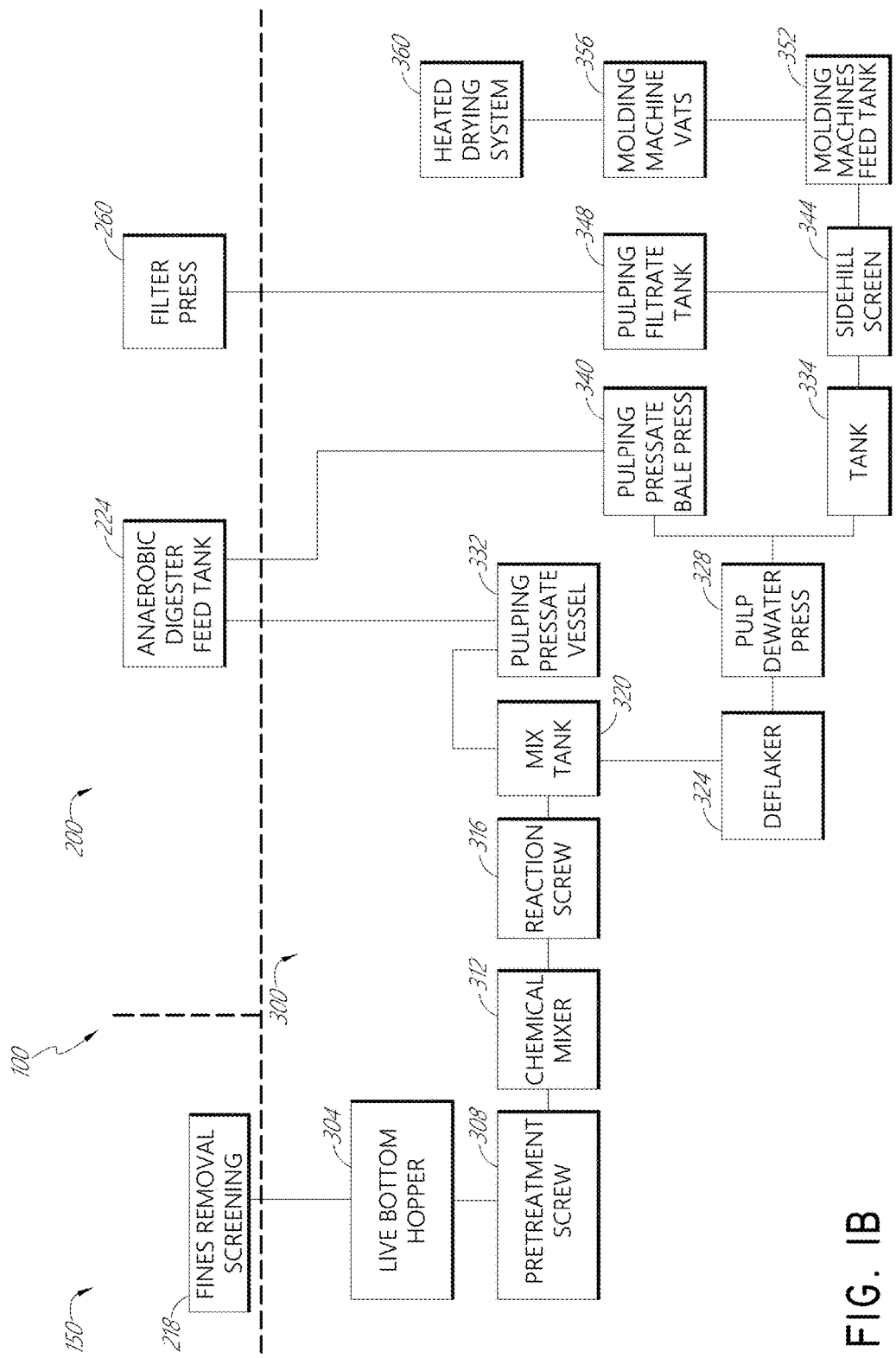
FIG. 1B is a schematic illustration of components of the system of FIG. 1A, showing mostly components of the solid pathway.

The following detailed description is directed to certain specific embodiments of the development. In this description, reference is made to the drawings wherein like parts or steps may be designated with like numerals throughout for clarity. Reference in this specification to "one embodiment," "an embodiment," or "in some embodiments" means that a particular feature, structure, or characteristic described in connection with the embodiment is included in at least one embodiment of the invention. The appearances of the phrases "one embodiment," "an embodiment," or "in some embodiments" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not others.

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the invention described herein.

Some terms or phrases used herein may be unfamiliar to the reader. Therefore, descriptions of these terms will be given. The following descriptions of certain terms are meant to assist with understanding the present disclosure. The descriptions are not meant to limit the disclosure but rather clarify the meaning of these terms as they are used herein.

Any examples given are merely illustrative and are not meant to limit the scope of the present disclosure. These descriptions will apply to the terms as used throughout the disclosure, unless the context in which they are used indicates otherwise. Furthermore, variations of these terms will also have the same description as the related term given below.

The term "juicing" is used herein in its ordinary sense as understood by those of skill in the art to refer to the process by which a liquid fraction is mechanically or physically removed from a solid agricultural crop.

The term "juiced crop" is used herein in its ordinary sense as understood by those of skill in the art to refer to the solid fraction following juicing.

The term "agricultural crop" is used herein in its ordinary sense as understood by those of skill in the art to refer to material harvested from plants grown on arable land. Agricultural crops or "crops" may include, but are not limited to, any grass type crop, millet, wheat, cane, sorghum, switch grass, and corn.

The term "dry harvest" is used herein in its ordinary sense as understood by those of skill in the art to refer to the process by which crops are chopped, then raked or collected in rows, allowed them to dry, and finally collected days or weeks later. The crops are typically baled, but may also be collected in piles.

The term "wet harvest" is used herein in its ordinary sense as understood by those of skill in the art to refer to a process by which an agricultural crop is harvested wet, collected and placed into either, but not limited to: piles, a pit, tubes, silos, or other conditions by which contact of oxygen with the product is minimized, such as in an ensilage process.

The term "ensilage" is used herein in its ordinary sense as understood by those of skill in the art to refer to a process by which, once crops are collected, oxygen is driven out to prevent degradation of organic materials that is commonly due to the presence of oxygen. This can be done with, but not limited to: piles, a pit, tubes, silos, or other conditions by which contact of oxygen with the product is minimized. This process can last days, weeks, months or even years.

The term "silage" is used herein in its ordinary sense as understood by those of skill in the art to refer to the product exiting the ensilage process.

The term "anaerobic digestion" is used herein in its ordinary sense as understood by those of skill in the art to refer to a process by which organic materials are converted by microbial action to methane ($CH_4$) and carbon dioxide ($CO_2$).

The term "pulping" is used herein in its ordinary sense as understood by those of skill in the art to refer to a process by which organic materials are treated with chemicals that allows fibrous compounds to be separated from lower value material. The fibrous compounds can then be used for paper, packaging, absorbency materials, or other similar products.

The term "filtrate" is used herein in its ordinary sense as understood by those of skill in the art to refer to the liquid fraction derived from a filtering process.

The term "pressate" is used herein in its ordinary sense as understood by those of skill in the art to refer to the liquid fraction derived from a pressing operation, such as a screw press or roll press. It may be used interchangeably with "juices," unless the context indicates otherwise.

The term "silage coverage" is used herein in its ordinary sense as understood by those of skill in the art to refer to any organic material that is on the surface of an ensilage pile that has become exposed to oxygen and begun the decomposition process due to the oxygen exposure.

The term "fines" is used herein in its ordinary sense as understood by those of skill in the art to refer to material that is smaller than the designated sieve, slot or hole size and that passes through a filtering media.

The term "nutrients" is used herein in its ordinary sense as understood by those of skill in the art to refer to compounds that an organism utilizes to survive and grow, which includes but is not limited to nitrogen, phosphorous, and potassium.

The term "methanogenic archaea" is used herein in its ordinary sense as understood by those of skill in the art to refer to microorganisms that produce methane as a metabolic byproduct in low or zero oxygen conditions. They are similar to bacteria, but found to be more ancient in origin.

The term "cure" is used herein in its ordinary sense as understood by those of skill in the art to refer to a process by which solids are allowed to cool down and reach and maintain a stable ambient temperature.

The term "cell burst" is used herein in its ordinary sense as understood by those of skill in the art to refer to a process by which cell walls of a plant material are ruptured utilizing heated water.

The term "grass crop" is used herein in its ordinary sense as understood by those of skill in the art to refer to a group of agricultural crops that are above ground. It may also be referred to simply as grasses. This includes, but is not limited to, sorghum, corn, arundo donax, giant reed, bamboo, sudan grass and wheat.

FIGS. 1A and 1B are schematic illustrations of different portions of an embodiment of a system 100 for pulping agricultural products. FIG. 1A shows details of the separation stage 150 and the liquid processing portion or liquid pathway 200, while FIG. 1B shows details of the solid processing portion or solid pathway 300. While the separation stage 150 and the two pathways 200, 300 may each be discussed separately, it is understood that they may be combined into one larger process and may interact with each other, as further described herein. Further, the classification of the system 100 into various portions or subsystems, such as the separation stage 150, the liquid pathway 200 and the solid pathway 300, is done merely for ease and convenience in describing the system 100. Such classification or division of the system 100 is approximate and does not provide definite boundaries in the system 100. Therefore, parts of the system 100, and the associated processes, may be described in the context of one or the other pathway, but it is understood that the parts and the associated processes may be considered to be part of both pathways. As an example, initial juicing systems and processes may be described in the context of the separation stage 150, but it is understood that such juicing systems and processes may also be considered to be part of the liquid pathway 200 and/or solid pathway 300. Thus, the division of the system 100 for the sake of description should not be read as limiting the scope of the present disclosure.

The system 100 may be used to produce pulping products as well as byproducts to be used in fuel or energy applications as well as fertilizers. In some embodiments, the system 100 is used to primarily produce paper products, and byproducts from system 100 are used for energy or fuel production and/or fertilizers.

Separation Stage

Referring to FIG. 1A, schematically illustrated components of embodiments of the separation stage 150 and the liquid pathway 200 are shown. In some embodiments, the system 100 includes the separation stage 150 connected to the liquid pathway 200 and the solid pathway 300. Components of the separation stage 150 will now be described, followed by detailed discussion of components of the liquid pathway 200 and the solid pathway 300.

In some embodiments, the separation stage 150 of the system 100 includes an ensilage facility 204. The agricultural crops used in system 100 may be grown as any other plant material and/or based on common regional practices and may be collected at the regionally determined harvest schedule. Harvesting of the crops may be performed utilizing ensilage specialized equipment. Upon harvesting of the crop, the materials are placed into the ensilage facility 204. In some embodiments, the ensilage facility is a pit. It may further be a pile, silo, or tube. The ensilage facility 204 may further comprise mechanisms for compacting the crops to minimize exposure of the crops to oxygen.

In some embodiments, the separation stage 150 of the system 100 includes a water bath 206. The water bath 206 may be connected to or otherwise coupled with the ensilage facility 204, such as by chute, conveyor, etc. The ensilaged crop, also known as silage, may be removed as needed from the ensilage facility 204 and sent to the water bath 206.

In some embodiments, the separation stage 150 includes a roll press 208. The roll press 208 may be connected to or otherwise coupled with the water bath 206, such as by chute, conveyor, etc. The silage may be sent from the water bath 206 to the roll press 208 for a first juicing or squeezing to remove liquid juices, or pressate. The first juicing in the roll press 208 extracts a certain portion of the liquid fraction of the silage. In some embodiments, the first juicing in the roll press 208 extracts between 20% and 80% of the liquids. The solids remaining after this first juicing are then typically, but not limited to, around 50% moisture.

In some embodiments, the separation stage 150 includes a fine separation 210. At the fine separation 210, the juiced solids may be screened to remove any fines that did not go out with the juice. Removal of fines increases the overall fiber length of the pulp product. Removal of fines also increases the overall beneficial characteristics of the pulp product.

In some embodiments, the separation stage 150 includes a rewetting stage 212. The rewetting stage 212 may be connected to or otherwise coupled with the roll press 208. After the liquids and fines are removed from the crop in the roll press 208 and fine separation 210, the solids are sent to the rewetting stage 212. In some embodiments, the solids are conveyed to the rewetting stage 212. In the rewetting stage 212, the solids are rewet. In some embodiments, the solids are rewetted with warm and/or hot water. In some embodiments, the water is eighty degrees Fahrenheit (80° F.) or more. In some embodiments, steam may also be used. The steam may help to speed up the process. In some embodiments, the rewetting stage 212 provides a cell burst, allowing nutrients tightly bound within the cell structure to be extracted. Cell burst exposes the nutrients held within the cell walls, such as the nucleus and membranes. Cell burst makes the pulping process more efficient and easier to work with by breaking down long cellulosic materials, which make up the cell wall. Organic materials extracted following the cell burst are primarily volatile solids which may carry little or no value to pulping, but they may carry high value for anaerobic digestion and energy production. In some embodiments, material leaving the rewetting stage 212 may be around eighty-five percent (85%) moisture. In some embodiments, the material leaving the rewetting stage 212 may be much more, or much less, than eighty-five percent (85%) moisture. When plant tissue is dried before cell burst, it is more difficult to convert to pulp. Further, minimal chemical injection is required to convert cell burst tissues to pulp as compared to those that are not cell burst.

In some embodiments, the separation stage 150 includes a roll press 216. The roll press 216 may be connected to the rewetting stage 212. In some embodiments, the roll press 216 is in addition to the roll press 208. In some embodiments, the roll press 216 is the same as the roll press 208 used before the rewetting stage 212, so that only one roll press is used to perform the two juicing operations. The rewetted solids from the rewetting stage 212 are subjected to the roll press 216 for another roll pressing process, which again extracts the liquids from the solids. This juicing step with the roll press 216 allows a greater percentage of the nutrients to be pulled from the solids.

In some embodiments, the separation stage 150 is connected to one or both of the liquid pathway 200 and solid pathway 300. In some embodiments, the pressate from the roll press 216 is combined with the pressate from the roll press 208. The pressate may then be sent to the liquid pathway 200 of the system 100. The system may include a fines removal screening 218. The screening 218 may be after the roll press 216. At the screening 218, the fines may be removed from the solution. In some embodiments, solids from the second stage pressing with the roll press 216 are sent to the solid pathway 300.

Liquids Pathway

Referring again to FIG. 1A, schematically illustrated components of an embodiment of the liquid pathway 200 of system 100 are shown. Components of the liquid pathway 200 will now be described, followed by detailed discussion of the solid pathway 300.

The liquid pathway 200 may include one or more hydrolysis tanks 220. In some embodiments, there are multiple hydrolysis tanks 220. As shown, the liquids from the roll press 208 and/or the roll press 216 in the separation stage 150 are discharged to the hydrolysis tank 220. In some embodiments, the liquid fractions, or pressates, from both juicing presses, i.e. the roll press 208 and the roll press 216, are pumped into the hydrolysis tank 220. The hydrolysis tank 220 may therefore be connected or otherwise coupled with the roll press 208 and/or the roll press 216. In some embodiments, piping allows for transport of the liquids and connects the hydrolysis tank 220 to one or both roll presses 208, 216.

In some embodiments, the hydrolysis tank 220 is a vessel or standpipe. The hydrolysis tank 220 may allow for the breakdown of organic material in the pressate to smaller organic chains. In some embodiments, organic material is broken down via bacterial consumption. In some embodiments, these smaller carbon chains or molecules are broken down by methanogenic organisms. In some embodiments, these smaller carbon chains or molecules are broken down by methanogenic archaea. In some embodiments, the smaller carbon chains are broken down into $CH_4$. In some embodiments, the smaller carbon chains are broken down primarily into $CH_4$. In some embodiments, the pH is raised in the hydrolysis tank 220. In some embodiments, the pH is raised slightly in the hydrolysis tank 220. The hydrolysis tanks 220 may be used for preparation of the pressate for anaerobic digestion.

Following the hydrolysis tank 220, the pressate may be transferred, such as by pumping, to an anaerobic digester feed tank 224. In the feed tank 224, the pressate may combine with other pressate or materials. In some embodiments, the pressate combines with pulp pressate, sorghum fines, sorghum silage coverage and/or any other organic wastes. In some embodiments, the pressate is combined with organic waste that is beneficial or useful for the purpose of energy production. The pH level in the feed tank 224 may be altered. In some embodiments, the pH level in the feed tank 224 is altered to levels suitable for methanogenic populations. In some embodiments, the pH level in the feed tank 224 is altered to a range of 6.2 to 7.8.

The anaerobic digester feed tank 224 may receive material from other sources. As shown, the feed tank 224 may receive the pulp pressate, sorghum fines, sorghum silage coverage and/or any other organic wastes from an organic waste storage 228. Further, the feed tank 224 may receive pulp pressate and/or other materials from the solid pathway 300. In some embodiments, pulp pressate and/or other materials are transferred from a pulping pressate vessel 332 and/or pulping pressate bale press 340 in the solid pathway 300. The storage 228, pulping pressate vessel 332, and/or pulping pressate bale press 340 may be connected to the feed tank 224 by piping or other suitable structures to pump or otherwise transfer contents therebetween.

The anaerobic digester feed tank 224 may be connected to a heat exchanger 232. In some embodiments, the anaerobic digester feed tank 224 is connected to the heat exchanger 232 by piping or other similar structure. Contents of the anaerobic digester feed tank 224 may be transferred to the heat exchanger 232 via the piping. In some embodiments, the contents are pumped therebetween. The heat exchanger may adjust the temperature of the contents to an optimal range for anaerobic digesters.

The heat exchanger 232 may be connected to an anaerobic digestion tank 236. In some embodiments, the heat exchanger 232 is connected to the anaerobic digestion tank 236 by piping or other suitable structure to transfer the contents therebetween. There may further be multiple anaerobic digestion tanks 236. In some embodiments, there are two, three, four or more anaerobic digestion tanks 236. After the heat exchanger 232, the contents may flow to the one or more anaerobic digestion tanks 236.

The content or feed slurry transferred to the anaerobic digestion tank 236 may contain solids. In some embodiments, the content has a range of three to fifteen percent (3-15%) solids. In the anaerobic digestion tank 236, methanogenic archaea may be allowed to function and process the organic materials further. In some embodiments, organic materials are processed into methane ($CH_4$). In some embodiments, organic materials are processed primarily into methane ($CH_4$).

The anaerobic digestion tank 236 may be connected, by piping or other suitable structure for transferring gases, to a gas cleaning stage 240. In some embodiments, anaerobic digestion in the anaerobic digestion tank 236 produces gases that are transferred to the gas cleaning stage 240 via the piping or other structure. In some embodiments, the anaerobic digestion tank 236 produces gases that include, but are not limited to, methane ($CH_4$), carbon dioxide ($CO_2$), and/or other minor gases. These gases may be captured at the surface of the tanks as they are produced. The gases may be transferred, such as pumped or otherwise piped, to the gas cleaning stage 240. The unwanted gases may be removed at the gas cleaning stage 240. In some embodiments, most of the unwanted gases may be removed at the gas cleaning stage 240. Cleaned gas may then be used for other purposes. In some embodiments, the cleaned gas is blown into an electrical generation system and/or compressed for use as compressed natural gas (CNG) and/or liquefied natural gas (LNG).

Feed material in the anaerobic digestion tank 236 may be retained for days, weeks, months, or longer, during which time gases may be collected as described above. In some embodiments, the feed material is retained in the anaerobic digestion tank 236 for fourteen (14) to twenty-eight (28) days. After the prescribed retention time, the contents, liquids, and suspended solids in the anaerobic digestion tank 236 may pass through a series of filters in order to maximize capture of nutrients and solids.

The anaerobic digestion tank 236 may be connected, by piping or other suitable structure for transferring its contents, to a drum filter 244, which may be a decker. In some embodiments, the contents are pumped to the drum filter 244. The drum filter 244 may alter the concentration of solids. In some embodiments, the drum filter 244 may increase the concentration of solids. In some embodiments, the drum filter 244 may increase the concentration of solids to around four to six percent (4-6%) solids.

The anaerobic digestion tank 236 may be connected, by piping or other suitable structure for transferring its contents, to a filter press 260. Solids from the anaerobic digestion tank 236 may discharge into a feed chute to the filter press 260. The filter press 260 may alter the concentration of solids. In some embodiments, the filter press 260 may increase the concentration of solids. In some embodiments, the filter press 260 may increase the concentration of solids to around four to six percent (4-6%) solids. The filter press 260 may compress the contents under very high pressure. In some embodiments, the filter press 260 is a membrane press. The filter press 260 may dewater the solids. In some embodiments, the solids are dewatered to around thirty to thirty-three percent (30-33%) solids.

The filter press 260 may remove suspended solids and/or nutrient compounds. In some embodiments, filter press 260 may remove around eighty percent (80%) of the suspended solids and from thirty to fifty percent (30-50%) of the nutrient compounds. In some embodiments, the filter press 260 may remove thirty to fifty percent (30-50%) of the major nutrient compounds, including nitrogen, phosphorous, potassium and/or others.

In some embodiments, the filter press 260 is connected to a molded fiber source 256. The molded fiber source 256 may contain contents from a molded fiber operation. Excess filtrate from the molded fiber operation may be pumped to the filter press 260.

The filter press 260 may be connected to an aerated conditioning drum 268 by piping or other suitable structure. Solids and nutrients from the filter press 260 may be conveyed into the aerated conditioning drum 268, which dries and conditions the finished product. The retention time of the solids and nutrients in the aerated conditioning drum 268 may be thirty (30) hours. Solids discharged from the aerated conditioning drum 268 may cure up to an additional three (3) days, or for a longer or shorter time period. The finished and cured product from the aerated conditioning drum 268 may then be shipped to the marketplace for use, resale, etc.

In some embodiments, the aerated conditioning drum 268 is connected to a curing system 270. Solids may be discharged from the aerated conditioning drum 268 to the curing system 270 to cure. The solids may cure in the curing system 270 up to three (3) days, or for a longer or shorter time period. The curing system may include a mechanical rotating drum, which may have flutes to help ensure flow. The drum may be elevated or sloped at between 0.5% and 2% grade depending on the size of the drum to ensure a 30-45 hour retention time. Other grades may be implemented. During the stay in the drum, air may be forced or otherwise put in at two or more separate intervals. This may maximize the allowance of oxygen for specific nitrifying bacteria to help expedite the maturing process of the fiber flowing through the drum.

The filter press 260 may further be connected to and receive filtrate or other materials from components in the solid pathway 300. In some embodiments, the filter press 260 is connected to and receives filtrate from a pulping filtrate tank 348 in the solid pathway 300. In some embodiments, the filter press 260 is connected to the pulping filtrate tank 348 by piping or other suitable structure.

The filter press 260 may further be connected to a zeolite filter 264. In some embodiments, the filter press 260 is connected to the zeolite filter 264 by piping or other suitable structure for transferring filtrate therebetween. In some embodiments, filtrate from the filter press 260 is pumped to the zeolite filter 264.

The zeolite filter 264 may be a zeolite filter system. The zeolite filter 264 may remove suspended solids and/or nutrient compounds from the fluid stream. In some embodiments, the zeolite filter 264 may remove suspended solids and/or nutrient compounds from the fluid stream by particle capture. In some embodiments, the zeolite filter 264 may remove a high percentage of both suspended solids and nutrient compounds from the fluid stream by particle capture. The zeolite filter 264 may be cleaned to force a chemical release of captured nutrients. In some embodiments, the zeolite filter 264 may be cleaned utilizing a potassium chloride solution to force a chemical release of nitrogen, phosphorous, potassium and/or other nutrient compounds.

Nutrients captured by the zeolite filter 264 may be classified separately from solid nutrients captured by the filter press 260. The solid nutrients captured by the filter press 260 may be classified as organic fertilizer. Nutrient compounds discharged from the zeolite filter 264 may be classified as a commercial chemical fertilizer. In some embodiments, nutrient compounds discharged from the zeolite filter 264 may be classified as a commercial chemical fertilizer due to the use of potassium chloride or other chemical cleaning solution.

Filtrate from the zeolite filter 264, now largely stripped of nutrients and suspended solids, may be recycled for dilution in other components of the liquid and/or solid pathways 200, 300. Excess filtrate may be pumped to a lagoon, where it may be stored for up to one hundred and eighty (180) days prior to being used for irrigation at agronomic application rates Solids Pathway Referring to FIG. 1B, schematically illustrated components of an embodiment of the solid pathway 300 of system 100 are shown. Juiced solids from the separation stage 150 may be transferred to the solid pathway 300, which may be a pulping facility. In some embodiments, juiced solids leaving the fines removal screening 218 of the separation stage 150 and/or liquid pathway 200 are conveyed to the solid pathway 300.

The solid pathway 300 may be connected or otherwise coupled to the separation stage 150 and/or liquid pathway 200 by conveyor, piping, or other suitable structure for transferring contents therebetween. In some embodiments, solids from the separation stage 150 and/or liquid pathway 200 are transferred onto a conveyor and then drop off into a live bottom hopper 304.

The live bottom hopper 304 may be connected or otherwise coupled to a pre-treatment screw 308 by conveyor, piping, or other suitable structure for transferring contents therebetween. In some embodiments, solids from the live bottom hopper 304 may be conveyed to the pre-treatment screw 308. In some embodiments, in the pre-treatment screw 308 the solids are combined with steam and strongly alkaline compounds. Such compounds may include, but are not limited to, Potash (KOH), caustic Soda (such as sodium hydroxide or NaOH), Lime ($Ca(OH)_2$), and/or combinations thereof The pre-treatment screw 308 may be connected or otherwise coupled to a chemical mixer 312 by conveyor, piping, or other suitable structure for transferring contents therebetween. In some embodiments, the pre-treatment screw 308 may discharge its contents to the chemical mixer 312. In some embodiments, the chemical mixer 312 may blend a hydrogen peroxide solution into the material discharged from the pre-treatment screw 308.

The chemical mixer 312 may be connected or otherwise coupled to a reaction screw 316 by conveyor, piping, or other suitable structure for transferring contents therebetween. In some embodiments, the chemical mixer 312 discharges to the reaction screw 316. In some embodiments, contents are retained in the reaction screw 316 for ten (10) to fifteen (15) minutes. In some embodiments, contents are retained in the reaction screw 316 for shorter or longer time periods.

The reaction screw 316 may be connected or otherwise coupled to a mix tank 320 by conveyor, piping, or other suitable structure for transferring contents therebetween. In some embodiments, the reaction screw 316 discharges contents to the mix tank 320. In some embodiments, reacted solids are blended with dilution water in the mix tank 320. In some embodiments, the dilution water may be clarified water from the zeolite filter 264, recirculated pulp pressate, and/or combinations thereof The mix tank 320 may be connected or otherwise coupled to a deflaker 324 by conveyor, piping, or other suitable structure for transferring contents therebetween. In some embodiments, contents of the mix tank 320 are pumped to the deflaker 324. In some embodiments, the deflaker 324 may break apart any larger pieces or lumps in the pulp.

The deflaker 324 may be connected or otherwise coupled to a pulp dewatering press 328 by conveyor, piping, or other suitable structure for transferring contents therebetween. In some embodiments, from the deflaker 324, the pulped solids flow to the pulp dewatering press 328. In some embodiments, the pulp dewatering press 328 may thicken the suspended solids. In some embodiments, the pulp dewatering press 328 may thicken the suspended solids to around thirty-three to thirty-seven percent (33%-37%) by weight. In some embodiments, the pulp dewatering press 328 may thicken the suspended solids to more or less than thirty-three to thirty-seven percent (33%-37%) by weight.

The pulp dewatering press 328 may be connected or otherwise coupled to a pulping pressate vessel 332, a pulping pressate bale press 340, and/or a tank 334 by conveyor, piping, or other suitable structure for transferring contents therebetween. In some embodiments, solids from the pulp dewatering press 328 discharge into a diversion chute. In some embodiments, the liquid squeezed from the pulp by the pulp dewatering press 328, called pressate, drops into the pulping pressate vessel 332, which may be a vessel, tank or standpipe. In some embodiments, the pulping pressate vessel 332 may be connected or otherwise coupled to the mix tank 320 by conveyor, piping, or other suitable structure for transferring contents therebetween. In some embodiments, from the pulping pressate vessel 332, some or all of the pressate may be pumped to the mix tank 320 as dilution for the pulp discharged from the reaction screw 316. In some embodiments, the pulping pressate vessel 332 may be connected or otherwise coupled to the anaerobic digester feed tank 224 in the liquid pathway 200 by conveyor, piping, or other suitable structure for transferring contents therebetween. In some embodiments, remaining pressate from the pulping pressate vessel 332 may be pumped to the anaerobic digester feed tank 224.

In some embodiments, one side of a diversion chute from the pulp dewatering press 328 leads to the pulping pressate bale press 340. In some embodiments, the bale press 340 compresses and/or dewaters the pulp. In some embodiments, the bale press 340 compresses and/or dewaters the pulp to around 50% suspended solids. In some embodiments, the bale press 340 compresses and/or dewaters the pulp to more or less than 50% suspended solids. In some embodiments, the bale press 340 may be connected or otherwise coupled to the anaerobic digester feed tank 224 in the liquid pathway 200 by conveyor, piping, or other suitable structure for transferring contents therebetween. In some embodiments, liquid discharged from the bale press 340, called pressate, is collected and pumped to the anaerobic digester feed tank 224.

In some embodiments, another side of the diversion chute from the pulp dewatering press 328 empties into the tank 334, which may be a vessel, tank or chest. In some embodiments, in the tank 334, pulp is diluted with clarified water from the zeolite filter 264. In some embodiments, in the tank 334, acid is added to adjust the pH of the pulp to a suitable value for molded fiber production.

The tank 334 may be connected or otherwise coupled to a sidehill screen 344 by conveyor, piping, or other suitable structure for transferring contents therebetween. In some embodiments, contents of the tank 334 may be pumped to the sidehill screen 344, which may be in a molded fiber area. In some embodiments, the sidehill screen 344 thickens the pulp to around four to five percent (4-5%) solids. In some embodiments, the sidehill screen 344 thickens the pulp to more or less than 4-5% solids.

The sidehill screen 344 may be connected or otherwise coupled to a molding machines feed tank 352 and/or a pulping filtrate tank 348 by conveyor, piping, or other suitable structure for transferring contents therebetween. In some embodiments, thickened pulp from the sidehill screen 344 discharges into the molding machines feed tank 352. In some embodiments, pulp in the molding machines feed tank 352 is diluted to around one percent (1%) solids. In some embodiments, pulp in the molding machines feed tank 352 is diluted to more or less than one percent (1%) solids. In some embodiments, filtrate from the sidehill screen 344 drops into a pulping filtrate tank 348, which may be a tank or standpipe. The pulping filtrate tank 348 may be connected or otherwise coupled to the filter press 260 of the liquid pathway 200 by conveyor, piping, or other suitable structure for transferring contents therebetween. In some embodiments, contents of the pulping filtrate tank 348 are pumped to the filter press 260, which may be in a water clarifying area of the liquid pathway 200.

The molding machines feed tank 352 may be connected or otherwise coupled to one or more molding machine vats 356 by conveyor, piping, or other suitable structure for transferring contents therebetween. In some embodiments, contents of the molding machines feed tank 352 are pumped to the molding machine vats 356. In some embodiments, screen mesh molds rotate through the molding machine vats 356. In some embodiments, the screen mesh molds collect a quantity of pulp slurry which may be drained by a combination of gravity and applied vacuum.

The molding machine vats 356 may be connected or otherwise coupled to a heated drying system 360 by conveyor, piping, or other suitable structure for transferring contents therebetween. In some embodiments, after enough water has been removed in the molding machine vats 356, the formed pulp passes into the heated drying system 360. In some embodiments, in the heated drying system 360, water is evaporated from the formed pulp. In some embodiments, in the heated drying system 360, water is evaporated from the formed pulp to a final moisture content of five to ten percent (5%-10%). In some embodiments, in the heated drying system 360, water is evaporated from the formed pulp to a final moisture content of more or less than five to ten percent (5%-10%).

In some embodiments, dried pulp in the desired form is discharged from the heated drying system 360. Molded fiber product may be trimmed to remove excess pulp from the form, which may be stacked and packaged for shipping.

Figure 2A:
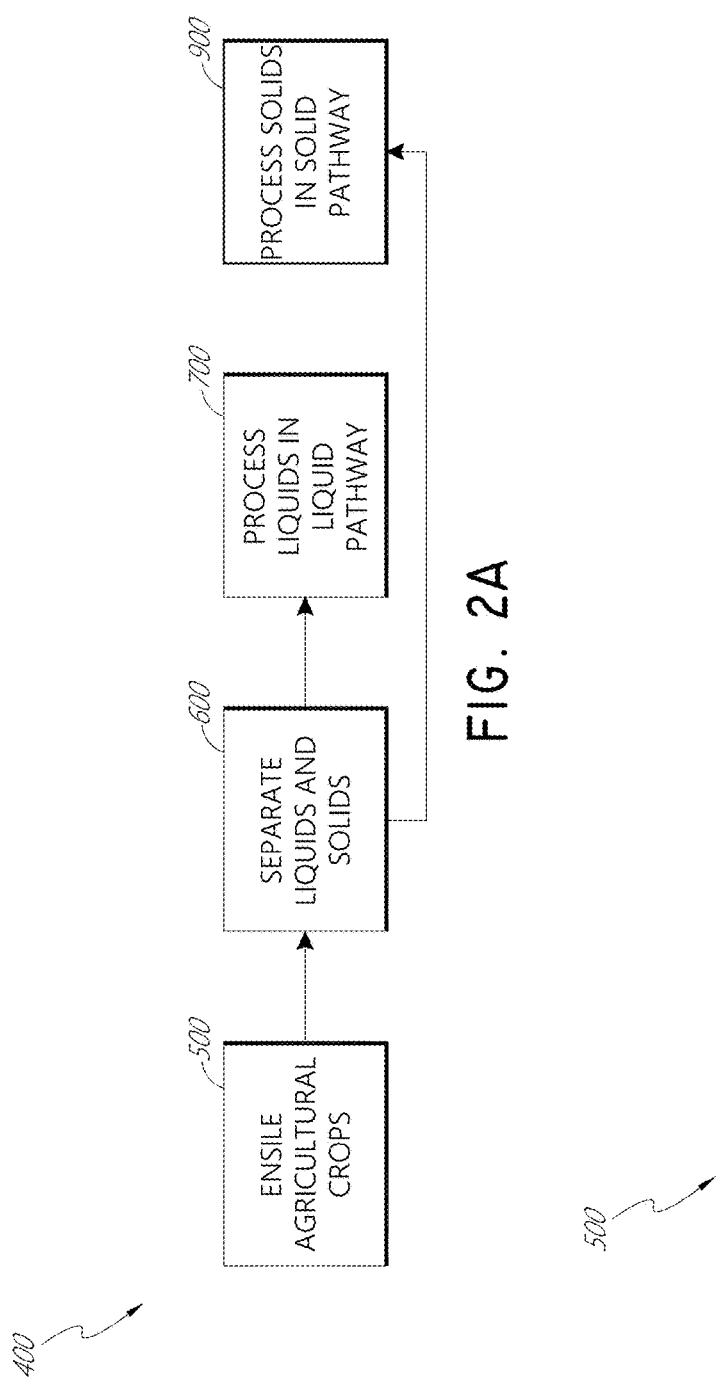
FIG. 2A is a flowchart showing an embodiment of an overview process for pulping agricultural products.

FIG. 2A is a flowchart showing an embodiment of an overview process 400 for pulping agricultural products. Details of the overview process 400 are further discussed below with reference to other figures, for example, FIGS. 2B-2E.

Referring to FIG. 2A, the process 400 may include step 500 wherein agricultural crops are ensiled or put into ensilage. In some embodiments, step 500 may include the separation stage 150, or portions thereof. In some embodiments, step 500 includes use of the ensilage facility 204.

The process 400 may further include step 600 wherein liquids and solids are separated. In some embodiments, step 600 may include the separation stage 150, or portions thereof. In some embodiments, step 600 may include use of the roll presses 208 and/or 216 as well as the fine separation 210, the rewetting stage 212 and/or the fines removal screening 218.

The process 400 may also include step 700 wherein liquids are processed in a liquid pathway. In some embodiments, step 700 may include the liquid pathway 200. In some embodiments, step 700 may include components of the liquid pathway 200 discussed herein, for example with respect to FIGS. 1A-1B.

The process 400 may also include step 900 wherein solids are processed in a solid pathway. In some embodiments, step 900 may include the solid pathway 300. In some embodiments, step 900 may include components of the solid pathway 300 discussed herein, for example with respect to FIG. 1A-1B. In some embodiments, solids separated in step 600 bypass step 700 and are processed in step 900 in the solid pathway.

Figure 2B:
FIG. 2B is a flowchart of part of the process of FIG. 2A showing a process for ensilage of agricultural crops.

FIG. 2B is a flowchart of part of an embodiment of a process 500 for ensilage of agricultural crops. The process 500 may be used in the overview process 400 discussed, for example, with respect to FIG. 2A.

Referring to FIG. 2B, the process 500 may include step 510 wherein agricultural crops are harvested. In some embodiments, harvest equipment is utilized for harvesting crops. This may be the same or similar equipment that is use for ensilage of animal feeds. In some embodiments, when the time comes to harvest a crop prior to storage, the equipment is brought in to the land where the agricultural crop has matured. This equipment may cut the crop starting at roughly, but not limited to, three (3) inches from the ground surface and chop and put it into trucks for transport to the ensilage location. The chopping size may be dictated by several factors. In some embodiments, the chopping size can range from mere millimeters in size to a couple inches in size, but it is not limited to these sizes.

The process 500 may further include step 520 wherein agricultural crops are placed into ensilage. In some embodiments, step 520 allows for the storage of both the solid and liquid fractions of the agricultural crop. Step 520 may allow, for example, for splitting the liquid and solid fractions. In some embodiments, in step 520 the liquid fraction may be used to produce energy. In some embodiment, in step 520 the solid fraction may be utilized for the production of pulp and fiber molded products.

Step 520 may be performed in a number of ways. In some embodiments, step 520 is performed with piles, silos, tubes, and/or pits, such as ground pits. In some embodiments, step 520 is done in anaerobic, i.e. oxygen-free, or low oxygen, environmental conditions. Anaerobic conditions may be created which prevent typical decomposition from occurring, either through biological means or through oxygen degradation.

In some embodiments, the ensilage of crops in step 520 may be used for pulping and energy production. In some embodiments, step 520 is used for the purpose of pulping of grass crops. In some embodiments, step 520 is used to store grass crops long term for the purpose of pulping production. In some embodiments, step 520 is used with wet agricultural crops to more easily process into pulp and more efficiently then dry agricultural crops, while permitting energy production from the liquid fraction. In some embodiments, step 520 is used to enables long term storage without significant biological decay of organic compounds to exposure to oxygen, while increasing sugar availability for purpose of energy production. In some embodiments, step 520 enables the long term storage without the risk of fire, due to high moisture content as compared to typical dry storage techniques. In some embodiments, step 520 enables the long term storage of grass crops without exposure to molds and fungi that typically plague dry storage techniques. In some embodiments, step 520 is a process that minimizes oxygen exposure to the agricultural crops for long term storage thus retarding and limiting oxidation or aerobic biological decomposition.

In some embodiments, a wet storage program via ensilage is used in step 520. This may prevent the accumulation of inorganics while minimizing the amount of decomposition that occurs and also minimizing the risk of fire or molds. Furthermore, ensilage of agricultural crops may allow for a one-step harvesting process and avoid risks that typically accompany dry harvest techniques.

The process 500 may also include step 530 wherein the crops are compacted. In some embodiments, in step 530 the crops are compacted to restrict oxygen influence and prevent oxygen flow from entering the pile, tube, silo, pit, or other ensilage means or facilities. This may allow for storage for days, months, or even years, allowing product to be used as needed. This permits the pulping facility to run year round, without the hindrance of seasonal rushes similar to those confronting the sugar industry or any other agricultural based industry that finds itself bound by a particular harvest window. Instead, the ability to pull regularly as needed, throughout the year, allows stability economically and provides increased operational viability, as opposed to the 2-3 month operating window that is typically needed.

Figure 2C:
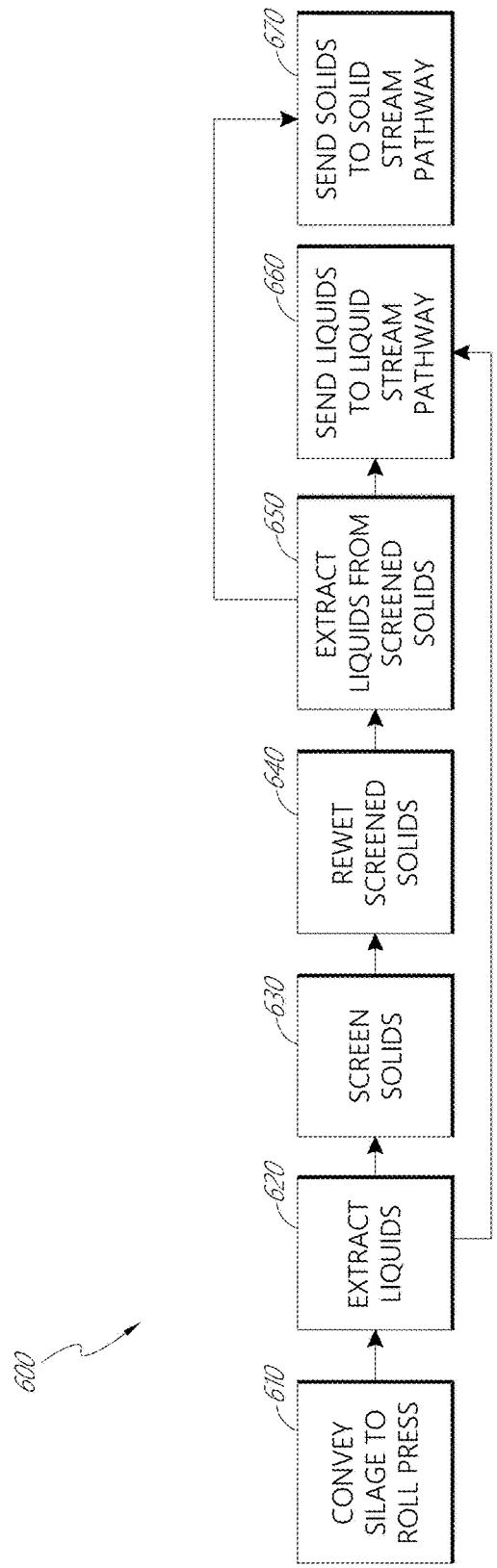
FIG. 2C is a flowchart of part of the process of FIG. 2A showing a process for separating solids and liquids in agricultural crops.

FIG. 2C is a flowchart of an embodiment of a process 600 for separating solids and liquids in agricultural crops. The process 600 may be used in the overview process 400 discussed, for example, with respect to FIG. 2A. In some embodiments, the separation of liquid from agricultural crops is done using mechanical or physical means. Further, process 600 may be used with components in the separation stage 150 discussed, for example, with respect to FIGS. 1A-1B.

The process 600 may include step 610 wherein silage is conveyed from an ensilage location to a mechanism for removing liquids. In some embodiments, the silage is conveyed from the ensilage facility 204 to the roll press 208. This may be done, for example, by conveyor belt, by hauling, or other ordinary conveyance methods. In some embodiments, wet or moist material is extracted from storage. In some embodiments, wet or moist silage is conveyed from the ensilage facility 204 to the roll press 208.

The process 600 may further include step 620 wherein liquids are extracted. In some embodiments, liquids are extracted from the silage. In some embodiments, the agricultural crop is placed in a juicing or pressing apparatus to extract or reduce the moisture that is within the agricultural crop materials. The liquids extracted in step 620 may then be sent to the liquid stream pathway, as shown in step 660 and discussed in further detail below.

The process 600 may also include step 630 wherein solids are screened. For agricultural products, screening is conventionally not performed, as the product is usually grown and maintained to levels desired by the pulp industry. However, screening has been found to have many benefits in the disclosed pulping process. Upon leaving the first juicing press, such as the roll press 208, the agricultural crop may be immediately screened utilizing a variety of screening technologies. In some embodiments, the agricultural crop may be screened using trammel screens, shaker screens, vibrating screens, and/or other means well known in the art. Different crop varieties may require different screening technologies based on the individual characteristics of each agricultural crop. In some embodiments, the purpose is to remove all fines that are less than three (3) millimeters (mm) in diameter. In some embodiments, solids are screened by using a fine mesh to filter out the solids. In some embodiments, fines are removed. Removal of fines may increase the overall fiber length of the pulp product and/or increase the overall beneficial characteristics of the pulp product.

The process 600 may further include step 640 wherein screened solids are rewetted. In some embodiments, the solids remaining after step 630 are placed in warm to hot water or steam and allowed to saturate. The time may vary from one plant material to another, which time may be determined by microscopic view of the plant material both before and after various temperatures and time exposures to cell burst processes.

Step 640 may include a cell burst process. Plant cells do not typically explode in water because they have cell walls. Their tendency to uptake water is balanced by the elastic wall pushing back on the cell, resulting in a turgid (rigid) cell rather than a lysed (exploded) cell. Turgid cells allow plants to stand upright and better engage in photosynthesis. Exposure under higher temperatures above ambient conditions weakens the elasticity of the cell wall. As the cell wall is raised in temperature the molecules radiate further apart, while the inside membrane remains at the same density, and the resulting difference creates a cell wall burst.

In some embodiments, a cell burst is performed using low to high temperature. In some embodiments, cell burst breaks open the cell of the plant cell. In some embodiments, cell burst exposes the nutrients held within the cell walls, such as the nucleus and membranes. In some embodiments, cell burst makes the pulping process more efficient and easier to work with by breaking down long cellulosic materials, which make up the cell wall. In some embodiments, juicing following the cell burst allows for high extraction of nutrients. In some embodiments, organic materials extracted following the cell burst are primarily volatile solids which carry no value to pulping, but carry high value for anaerobic digestion and energy production In some embodiments, the solids are exposed to warm or hot water to explode the cellular walls in the plant tissue. The temperature may be as low as eighty-five degrees Fahrenheit (85° F.) to begin the cell wall explosion in plant tissue. In some embodiments, the cell burst process is done at roughly one hundred and ten degrees Fahrenheit (110° F.). The cell burst process at roughly one hundred and ten degrees Fahrenheit (110° F.) may be instantaneous. In some embodiments, the cell burst allows for maximum nutrient and inorganic removal from plant tissue cells. In some embodiments, cell Burst plant tissue weakens the lignin and cellulose structures in preparation for pulp production. In some embodiments, cell burst is performed while plant tissue is maintained wet or moist. In some embodiments, plant tissue following cell explosion or cell burst is easier drained of moisture when the cell wall is broken. In some embodiments, following cell burst more volatile and suspended solids are removed increasing potential energy value of the liquid stream that is extracted from the plant tissue. In some embodiments, cell burst can occur at lower temperatures (e.g. eighty-five degrees Fahrenheit (85° F.) or lower) but performs faster at higher temperatures. In some embodiments, when plant tissue is dried before cell burst, it is more difficult to convert to pulp. In some embodiments, minimal chemical injection is required to convert cell burst tissues to pulp as compared to those that are not cell burst.

The process 600 may also include step 650 wherein liquids are extracted from the screened solids. In some embodiments, the screened solids are again placed through a juicing or pressing apparatus which once again removes the available nutrients, which at this point also includes those nutrients and soluble solids that were contained within the cell itself. In some embodiments, upon leaving the cellular burst bath, moisture is ranging from sixty to ninety percent (60% to 90%) and the solids are again pressed or juiced to remove this new moisture, along with all nutrients and loose minerals and highly volatile solids within the plant cell walls, such as the now exposed nucleus and membranes. In some embodiments, the second pass extraction or juicing brings the solids down to less than fifty-five percent (55%) moisture and makes them highly suitable for pulping.

The process 600 may also include step 660 wherein the liquids are sent to a liquid stream pathway. These may be liquids remaining from step 650 after liquids are extracted from the screened solids. These may also be liquids extracted in step 620. In some embodiments, the liquid stream pathway is the liquid pathway 200.

The process 600 may also include step 670 wherein the solids are sent to a pulping facility. These may be solids remaining after step 650 wherein the liquids are extracted. In some embodiments, solids are sent to the solid pathway 300.

Figure 2D:
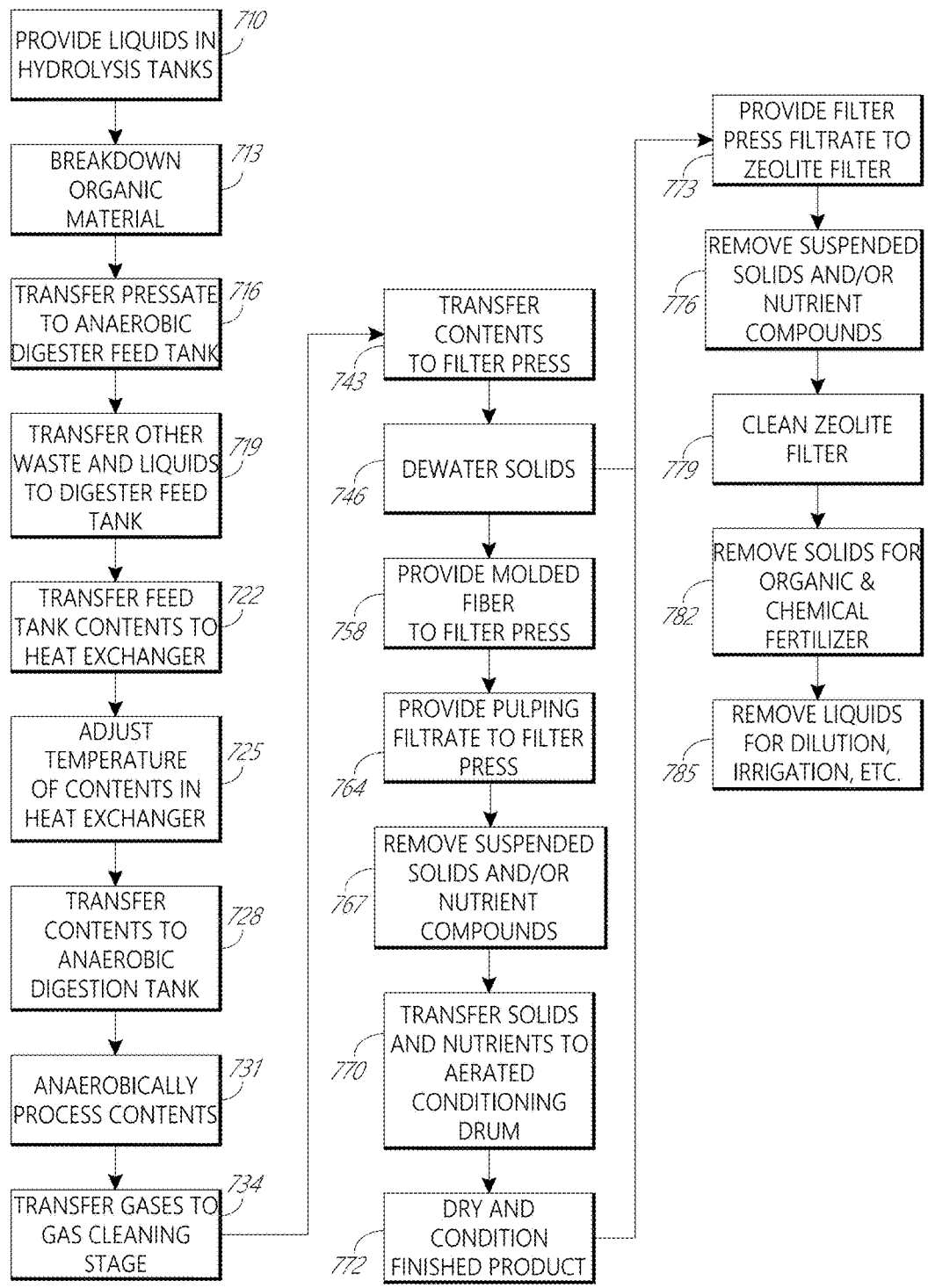
FIG. 2D is a flowchart of part of the process of FIG. 2A showing a process for processing liquids using the liquid pathway components shown in FIGS. 1A-1B.

FIG. 2D is a flowchart of an embodiment of a process 700 for processing liquids. The process 700 may be done primarily using components from the liquid pathway 200 and/or separation stage 150, which components are discussed, for example, with respect to FIGS. 1A and 1B. Components from the solid pathway 300 may also be utilized in the process 700. Various embodiments of steps that may be included in the process 700 will now be discussed. However, it is understood that other details and steps related to process 700 are further discussed herein, for example with respect to FIGS. 1A-1B.

The process 700 may include step 710 wherein liquids are provided in one or more hydrolysis tanks. In some embodiments, the liquids are pumped from one or more roll presses into the hydrolysis tanks. For instance, liquids from the roll press 208 and/or the roll press 216 may be pumped to the hydrolysis tank 220.

The process 700 may further include step 713 wherein organic material is broken down. In some embodiments, organic material is broken down via bacterial consumption, with methanogenic organisms, and/or with methanogenic archaea into $CH_4$. Step 713 may further include adjusting the pH level of the contents of the hydrolysis tanks. In some embodiments, the pH level is raised in step 713. Step 713 may further include preparation of the pressate for anaerobic digestion.

The process 700 may further include step 716 wherein pressate is transferred from one or more hydrolysis tanks to one or more anaerobic digester feed tanks. In some embodiments, the pressate is pumped. For instance, the pressate may be pumped from the hydrolysis tank 220 to the anaerobic digester feed tank 224. Step 716 may further include combining the pressate with other pressate or materials and/or adjusting the pH level in the feed tank 224.

The process 700 may further include step 719 wherein other waste and/or liquids are transferred to a feed tank. In some embodiments, organic waste is pumped from the organic waste storage 228 to the feed tank 224. In some embodiments, liquids from the solid pathway 300 are transferred to the feed tank 224. For example, liquids from the pulping pressate vessel 332 and/or pulping pressate bale press 340 may be transferred to the feed tank 224.

The process 700 may further include step 722 wherein contents of a feed tank are transferred to a heat exchanger. In some embodiments, contents of the feed tank 224 are pumped to the heat exchanger 232.

The process 700 may further include step 725 wherein the temperature of contents in the heat exchanger is adjusted.

The process 700 may further include step 728 wherein contents of a heat exchanger are transferred to one or more anaerobic digestion tanks. In some embodiments, the contents flow from the heat exchanger 232 to the one or more anaerobic digestion tanks 236.

The process 700 may further include step 731 wherein contents of an anaerobic digestion tank or tanks are processed. In some embodiments, methanogenic archaea are allowed to function and process the organic materials, such as solids, into methane. In some embodiments, contents are retained in the anaerobic digestion tank for a period of time, including but not limited to two (2) to four (4) weeks.

The process 700 may further include step 734 wherein gases from an anaerobic digestion tank or tanks are transferred to a gas cleaning stage. In some embodiments, gases from the anaerobic digestion tank 236 are piped to the gas cleaning stage 240 from the surface of the digestion tank 236. Step 734 may further include removing the gases from the gas cleaning stage and using them for other purposes, such as blowing them into an electrical generation system and/or compressing them for use as compressed natural gas (CNG) and/or liquefied natural gas (LNG).

The process 700 may further include step 743 wherein contents of an anaerobic digestion tank are transferred to a filter press. In some embodiments, solids from the anaerobic digestion tank 236 may discharge into a feed chute to the filter press 260. In some embodiments, the concentration of solids is altered. In some embodiments, the concentration of solids may be increased to around four to six percent (4-6%) solids.

The process 700 may further include step 746 wherein solids are dewatered. In some embodiments, the solids are dewatered to around thirty to thirty-three percent (30-33%) solids.

The process 700 may further include step 758 wherein molded fiber is provided to a filter press. In some embodiments, molded fiber from the molded fiber source 256 is transferred to the filter press 260. In some embodiments, excess filtrate from a molded fiber operation may be pumped to the filter press 260. In some embodiments, excess filtrate is pumped to the filter press 260 from the molded fiber source 256.

The process 700 may further include step 764 wherein pulping filtrate may be transferred to a filter press. In some embodiments, filtrate is pumped to the filter press 260 from the pulping filtrate tank 348 in the solid pathway 300.

The process 700 may further include step 767 wherein suspended solids and/or nutrient compounds are removed. In some embodiments, suspended solids and/or nutrients are removed in a filter press, such as the filter press 260. In some embodiments, around eighty percent (80%) of the suspended solids are removed by the filter press 260. In some embodiments, more or less than eighty percent (80%) of the suspended solids are removed by the filter press 260. In some embodiments, from thirty to fifty percent (30-50%) of the nutrient compounds are removed by the filter press 260. In some embodiments, the filter press 260 may remove thirty to fifty percent (30-50%) of the major nutrient compounds, including nitrogen, phosphorous, potassium and/or others. In some embodiments, more or less than thirty to fifty percent (30-50%) of the nutrient compounds are removed by the filter press 260.

The process 700 may further include step 770 wherein solids and/or nutrients are transferred to an aerated conditioning drum. In some embodiments, solids and nutrients from the filter press 260 may be conveyed into the aerated conditioning drum 268.

The process 700 may further include step 772 wherein the finished product is dried and/or conditioned. In some embodiments, solids and nutrients are retained in an aerated conditioning drum for drying, conditioning, etc. In some embodiments, solids and nutrients are retained in the aerated conditioning drum for thirty (30) hours. In some embodiments, solids and nutrients are retained in the aerated conditioning drum for longer or shorter than thirty (30) hours. Step 772 may further include discharge of solids from the aerated conditioning drum 268 to cure up to an additional three (3) days, or for a longer or shorter time period. The solids may be discharged to the curing system 270.

The process 700 may further include step 773 wherein filtrate from a filter press is provided to a zeolite filter. In some embodiments, filtrate from the filter press 260 is pumped to the zeolite filter 264.

The process 700 may further include step 776 wherein suspended solids and/or nutrients are removed in a zeolite filter. In some embodiments, the zeolite filter 264 may remove various amounts of suspended solids and/or nutrient compounds from the fluid stream by particle capture.

The process 700 may further include step 779 wherein a zeolite filter is cleaned. In some embodiments, the zeolite filter 264 may be cleaned to force a chemical release of captured nutrients. In some embodiments, the zeolite filter 264 may be cleaned utilizing a potassium chloride solution to force a chemical release of nitrogen, phosphorous, potassium and/or other nutrient compounds.

The process 700 may further include step 782 wherein solids are removed from a zeolite filter or filter press for use as or in organic and/or chemical fertilizer. In some embodiments, solids are discharged from the zeolite filter 264 and/or the filter press 260.

The process 700 may further include step 785 wherein liquids are removed for dilution, irrigation, and/or other purposes. In some embodiments, filtrate from the zeolite filter 264 may be recycled for dilution in other components of the liquid and/or solid pathways 200, 300. In some embodiments, excess filtrate may be pumped to a lagoon. In some embodiments, excess filtrate is removed and stored for up to one hundred and eighty (180) days prior to being used for other purposes, such as irrigation at agronomic application rates, etc.

Figure 2E:
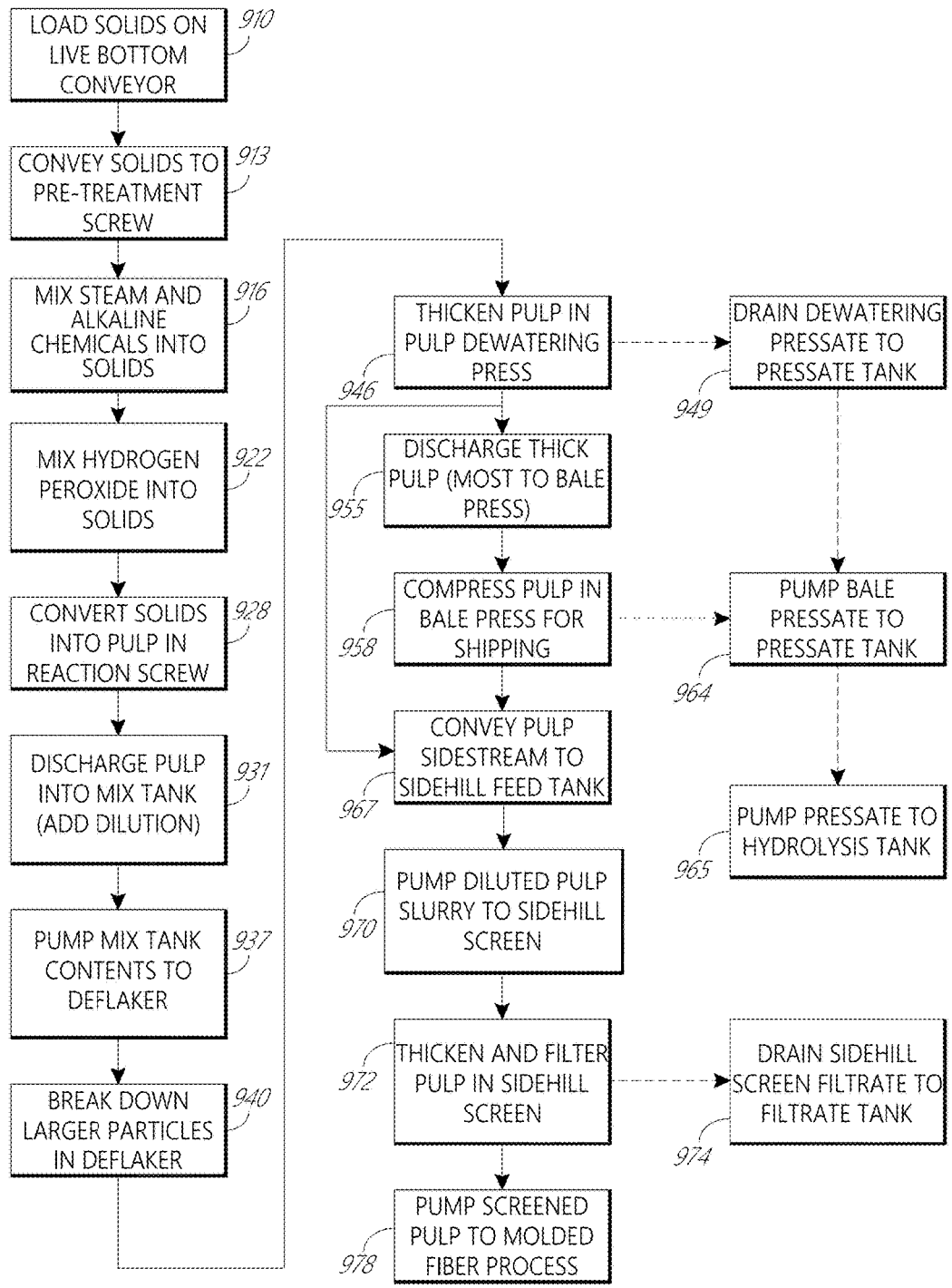
FIGS. 2E-2F are flowcharts of part of the process of FIG. 2A showing a process for processing solids using the solid pathway components shown in FIGS. 1A-1B.
Figure 2F:
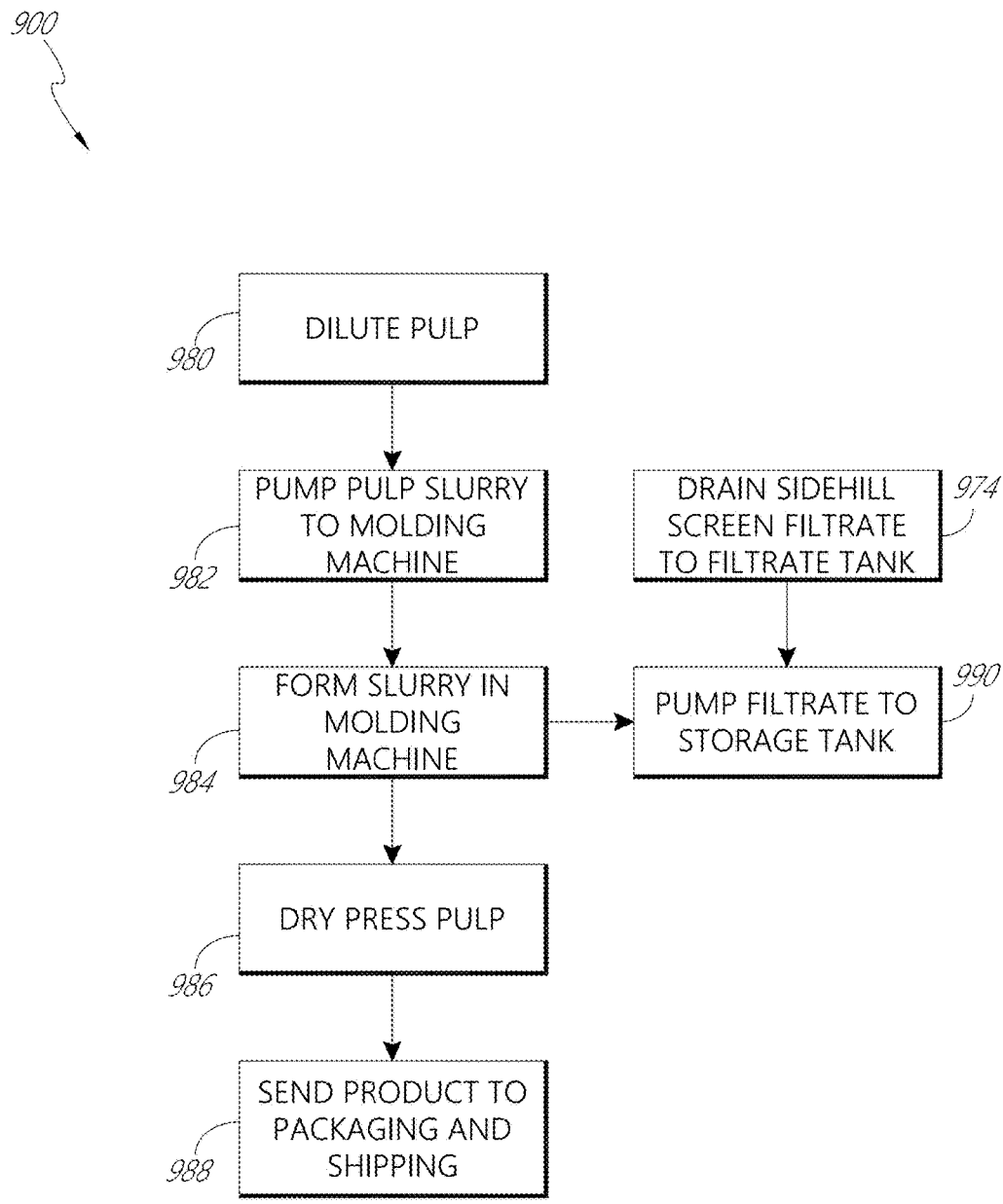

FIGS. 2E and 2F are flowcharts of part of the process 900 of FIG. 2A showing processes for processing solids. The process 900 may be done using components from the solid pathway 300 and/or separation stage 150, which components are discussed, for example, with respect to FIGS. 1A and 1B. Various embodiments of steps that may be included in the process 900 will now be discussed. However, it is understood that other details and steps related to process 900 are further discussed herein, for example with respect to FIGS. 1A-1B.

Referring to FIG. 2E, an embodiment of the process 900 may include step 910 wherein solids are provided to a live bottom conveyor. In some embodiments, solids are loaded from a roll press in other stages or pathways to the live bottom conveyor. For example, solids may be loaded from the roll press 216, in the separation stage 150 and/or in the liquid pathway 200, to the live bottom hopper 304.

The process 900 may further include step 913 wherein solids are transferred to a pre-treatment screw. In some embodiments, solids from the live bottom hopper 304 may be conveyed to the pre-treatment screw 308.

The process 900 may further include step 916 wherein solids in the pre-treatment screw are mixed or otherwise combined with steam and strongly alkaline compounds. In some embodiments, solids in the pre-treatment screw may be combined with Potash (KOH), caustic Soda (NaOH), Lime ($Ca(OH)_2$), combinations thereof, and/or other compounds. In some embodiments, these or other compounds are combined with heat. In some embodiments, strongly alkaline inorganic bases are added along with heat to start hydrolyzing the complex organic compounds in agricultural crop feedstock. In some embodiments, calcium hydroxide, potassium hydroxide and/or sodium hydroxide are added.

The process 900 may further include step 922 wherein hydrogen peroxide is mixed into the solids. In some embodiments, hydrogen peroxide is blended into hot, alkalized feedstock to break down organic binders and release the fibrous cellulose that constitutes pulp. Steps 916 and/or 922 may be done, for example, in the chemical mixer 312. In some embodiments, the pre-treatment screw 308 may discharge its contents to the chemical mixer 312.

The process 900 may further include step 928 wherein contents are reacted in a reaction screw. In some embodiments, the chemical mixer 312 discharges contents to the reaction screw 316. In some embodiments, the solids are converted into pulp in the reaction screw 316. In some embodiments, contents are retained and reacted in the reaction screw 316 for ten (10) to fifteen (15) minutes. In some embodiments, contents are retained and reacted in the reaction screw 316 for shorter or longer time periods.

The process 900 may further include step 931 wherein contents of a reaction screw are transferred to a mix tank. In some embodiments, the reaction screw 316 discharges the pulp contents to the mix tank 320. In some embodiments, the reacted solids are blended with dilution water in the mix tank 320. In some embodiments, the dilution water may be clarified water from the zeolite filter 264, recirculated pulp pressate, combinations thereof, and/or other liquids or liquid sources.

The process 900 may further include step 937 wherein contents of a mix tank are transferred to a deflaker. In some embodiments, contents of the mix tank 320 are pumped to the deflaker 324.

The process 900 may further include step 940 wherein large pieces are broken down in a deflaker. In some embodiments, the deflaker 324 may break apart any larger pieces or lumps in the pulp.

The process 900 may further include step 946 wherein suspended solids are thickened. In some embodiments, pulped solids from the deflaker 324 flow to the pulp dewatering press 328. In some embodiments, the pulp dewatering press 328 may thicken the suspended solids. In some embodiments, the pulp dewatering press 328 may thicken the suspended solids to more, less or around thirty-three to thirty-seven percent (33%-37%) by weight.

The process 900 may further include step 949 wherein the dewatering pressate is drained to a pressate tank. The dashed lines between step 946 and step 949 indicate that this may be a side process. The solid lines between other steps indicate those steps are part of a main process. These indications are for clarity only and do not limit the scope of the present disclosure. In some embodiments, liquid squeezed from the pulp by the pulp dewatering press 328 drops into the pulping pressate vessel 332.

The process 900 may further include step 955 wherein thick pulp is discharged. Most of the thick pulp may be discharged to a bale press. In some embodiments, pulp from the pulp dewatering press 328 is lead through one side of a diversion chute to the pulping pressate bale press 340. In some embodiments, pressate is transferred from a pulping pressate vessel to a mix tank and/or an anaerobic digester feed tank. In some embodiments, some or all of the pressate from the pulping pressate vessel 332 may be pumped to the mix tank 320 as dilution for the pulp discharged from the reaction screw 316. In some embodiments, pressate from the pulping pressate vessel 332 may be pumped to the anaerobic digester feed tank 224 in the liquid pathway 200.

The process 900 may further include step 958 wherein pulp is compressed in a bale press for shipping. In some embodiments, the bale press 340 compresses and/or dewaters the pulp to more than, less than or around 50% suspended solids.

The process 900 may further include step 964 wherein bale pressate is pumped to a pressate tank. In some embodiments, pulp is emptied into the tank 334 through a side of a diversion chute from the pulp dewatering press 328.

The process 900 may further include step 965 wherein pressate is pumped or otherwise transferred to a hydrolysis tank.

The process 900 may further include step 967 wherein pulp sidestream is conveyed to a sidehill feed tank. In some embodiments, the pulp is diluted and/or the pH is adjusted. In some embodiments, pulp is diluted in the tank 334 with clarified water from the zeolite filter 264 of the liquid pathway 200. In some embodiments, acid is added to the tank 334 to adjust the pH of the pulp to a suitable value for molded fiber production.

The process 900 may further include step 970 wherein the diluted pulp slurry is transferred to a sidehill screen. In some embodiments, contents of the tank 334 may be pumped to the sidehill screen 344.

The process 900 may further include step 972 wherein pulp is thickened and filtered. In some embodiments, pulp is thickened and filtered in a sidehill screen. In some embodiments, the sidehill screen 344 thickens the pulp to more than, less than or around four to five percent (4-5%) solids.

The process 900 may further include step 974 wherein the sidehill screen filtrate is drained from a sidehill screen to a filtrate tank. In some embodiments, filtrate from the sidehill screen 344 drops into the pulping filtrate tank 348.

The process 900 may further include step 976 wherein filtrate in a pulping filtrate tank is transferred to a filter press. In some embodiments, contents of the pulping filtrate tank 348 are pumped to the filter press 260. In some embodiments, the filter press 260 is in a water clarifying area of the liquid pathway 200.

The process 900 may further include step 978 wherein screened pulp is pumped or otherwise transferred to a molded fiber process. In some embodiments, thickened pulp from the sidehill screen 344 discharges into the molding machines feed tank 352.

The process 900 discussed with respect to FIG. 2E may include further steps. Some of those steps are discussed with respect to FIG. 2F.

Referring now to FIG. 2F, the process 900 may further include step 980 wherein pulp is diluted in a molding machines feed tank. In some embodiments, pulp in the molding machines feed tank 352 is diluted to more than, less than or around one percent (1%) solids.

The process 900 may further include step 982 wherein pulp slurry is pumped to a molding machine. In some embodiments, the contents of a molding machines feed tank are transferred to one or more molding machine vats. In some embodiments, contents of the molding machines feed tank 352 are pumped to the molding machine vats 356.

The process 900 may further include step 984 wherein slurry is formed in the molding machine. In some embodiments, screen mesh molds in the molding machine vats 356 collect the pulp slurry. In some embodiments, the pulp slurry may be drained by gravity, applied vacuum, and/or combinations thereof The process 900 may further include step 990 where the filtrate is pumped to a storage tank. Step 990 may also follow step 974 where the sidehill screen filtrate is drained to the filtrate tank. Both sources may supply the filtrate that is pumped to the storage tank.

The process 900 may further include step 986 wherein the pulp is dry pressed. In some embodiments, formed pulp passes from the molding machine vats 356 into the heated drying system 360. In some embodiments, formed pulp passes into the heated drying system 360 after enough water has been removed in the molding machine vats 356. In some embodiments, water is evaporated in the heated drying system 360 from the formed pulp. In some embodiments water is evaporated in the heated drying system 360 from the formed pulp to a final moisture content of more than, less than or around five to ten percent (5%-10%). In some embodiments, dried pulp in the desired form is removed, grabbed, taken or otherwise discharged from the heated drying system 360.

The process 900 may further include step 992 wherein the pulp product is packaged and shipped. In some embodiments, molded fiber product may be trimmed to remove excess pulp from the form, which may be stacked and packaged for shipping.

Although this invention has been disclosed in the context of certain embodiments and examples, it will be understood by those skilled in the art that the present invention extends beyond the specifically disclosed embodiments to other alternative embodiments and/or uses of the invention and apparent modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Further, while certain processes or methods have been discussed, the order of discussion of such steps or features of those processes and methods should not be read as limiting the order of performing the steps or features of the methods or processes. Thus, it is intended that the scope of the present invention herein disclosed should not be limited by the particular disclosed embodiments described above, but should be determined only by a fair reading of the claims that follow.

What is claimed is:

1. An ensilage system for pulping agricultural crop, the system comprising:
   an ensilage facility configured to store the crop;
   a separation stage coupled with the ensilage facility, the separation stage configured to receive the crop from the ensilage facility and to separate solids from liquids in the crop, wherein the separation stage comprises a first roll press configured to compress wet crop and thereby separate liquids from the crop, a rewetting after the first roll press and a second roll press coupled after the rewetting stage and configured to receive and compress the wet crop and thereby further separate liquids from the crop;
   a liquids pathway coupled with the separation stage and configured to receive the liquids separated in the separation stage and to process the liquids for energy production; and
   a solids pathway coupled with the separation stage and configured to receive the solids separated in the separation stage and to process the solids into pulping product.

2. The system of claim 1, wherein the ensilage facility is further configured to compact the crop.

3. The system of claim 1, wherein the ensilage facility is further configured to minimize oxygen exposure to the crop.

4. The system of claim 1, wherein the separation stage further comprises a water bath coupled with the ensilage facility and configured to wet the crop.

5. The system of claim 1, wherein the first roll press is coupled with a hydrolysis tank in the liquid pathway and is further configured to convey the separated liquids to the hydrolysis tank.

6. The system of claim 1, wherein the separation stage further comprises a fines removal screening component coupled after the second roll press and configured to remove fines in the crop by screening.

7. The system of claim 1, wherein the separation stage further comprises a moisture removal component configured to remove one or more of moisture, fines and inorganic fraction of the crop.

8. The system of claim 1, wherein the second roll press follows a cell burst in the rewetting stage to allow for high extraction of nutrients from the crop.

9. The system of claim 1, wherein the separation stage further comprises a fine separation component coupled after the first roll press and configured to receive the crop from the first roll press and to separate fine solids from the crop.

10. The system of claim 9, wherein the rewetting stage is coupled with the fine separation component and configured to receive the crop from the fine separation component and to rewet the crop.

11. An ensilage system for pulping agricultural crop, the system comprising:
    an ensilage facility configured to store the crop;
    a separation stage coupled with the ensilage facility, the separation stage configured to receive the crop from the ensilage facility and to separate solids from liquids in the crop;
    a liquids pathway configured to receive the liquids separated in the separation stage and to process the liquids for energy production, wherein the liquid pathway further comprises:
      a hydrolysis tank coupled with the separation stage;
      an anaerobic digester feed tank coupled with the hydrolysis tank;
      an anaerobic digestion tank coupled with the hydrolysis tank;
      a filter press coupled with the anaerobic digestion tank; and
      an aerated conditioning drum coupled with the filter press; and
    a solids pathway coupled with the separation stage and configured to receive the solids separated in the separation stage and to process the solids into pulping product.

12. The system of claim 11, wherein the liquid pathway further comprises an organic waste storage coupled with the anaerobic digester feed tank.

13. The system of claim 11, wherein the liquid pathway further comprises a gas cleaning stage coupled with the anaerobic digestion tank.

14. The system of claim 11, wherein the liquid pathway further comprises a curing system coupled with the aerated conditioning drum.

15. The system of claim 11, wherein the liquid pathway further comprises a molded fiber source coupled with the filter press.

16. The system of claim 11, wherein the liquid pathway further comprises a zeolite filter coupled with the filter press.

17. The system of claim 11, further comprising a heat exchanger coupled with the anaerobic digester feed tank.

18. An ensilage system for pulping agricultural crop, the system comprising:
    an ensilage facility configured to store the crop;
    a separation stage coupled with the ensilage facility, the separation stage configured to receive the crop from the ensilage facility and to separate solids from liquids in the crop;
    a liquids pathway coupled with the separation stage and configured to receive the liquids separated in the separation stage and to process the liquids for energy production; and
    a solids pathway coupled with the separation stage and configured to receive the solids separated in the separation stage and to process the solids into pulping product,
    wherein the solids pathway comprises:
      a pretreatment vessel configured to combine the solids with steam and alkaline compounds; and a storage tank configured to adjust the pH of pulp, wherein the storage tank is configured to dilute the pulp with clarified water from a zeolite filter.

19. The system of claim 18, wherein the storage tank is configured to adjust the pH of the pulp to a suitable value for molded fiber production.

20. The system of claim 18, further comprising a live bottom hopper coupled with the separation stage and configured to receive solids from the separation stage, wherein the pretreatment vessel is configured to receive the solids from the live bottom hopper.

21. The system of claim 18, further comprising a chemical mixer coupled with the pretreatment vessel and configured to receive the solids from the pretreatment vessel.

22. The system of claim 18, further comprising a reaction vessel in which the solids are converted into pulp.

23. The system of claim 22, further comprising a mix tank coupled with the reaction vessel and configured to receive the pulp from the reaction vessel.

24. The system of claim 18, further comprising a deflaker.

25. The system of claim 18, further comprising a pulp dewater press.

26. The system of claim 18, further comprising a sidehill screen coupled with the storage tank configured to receive the solids from the storage tank.

27. The system of claim 26, further comprising one or more molding machines feed tanks coupled with the sidehill screen and configured to receive the solids from the sidehill screen.

28. The system of claim 27, further comprising one or more molding machine vats coupled with the one or more molding machines feed tanks and configured to receive the solids from the one or more molding machines feed tanks.

* * * * *